(12) United States Patent
Lampropoulos et al.

(10) Patent No.: US 8,951,270 B2
(45) Date of Patent: Feb. 10, 2015

(54) SURGICAL SECUREMENT SYSTEM AND APPARATUS

(75) Inventors: Fred P. Lampropoulos, Salt Lake City, UT (US); Timothy W. Clark, Philadelphia, PA (US); Gregory R. McArthur, Sandy, UT (US)

(73) Assignee: Marit Medical Systems, Inc., South Jordan, UT (US)

( * ) Notice: Subject to any disclaimer, the term of this patent is extended or adjusted under 35 U.S.C. 154(b) by 1065 days.

(21) Appl. No.: 12/202,073

(22) Filed: Aug. 29, 2008

(65) Prior Publication Data

US 2010/0057110 A1    Mar. 4, 2010

(51) Int. Cl.
| A61B 17/04 | (2006.01) |
| A61B 17/06 | (2006.01) |
| A61B 19/00 | (2006.01) |
| A61B 17/02 | (2006.01) |

(52) U.S. Cl.
CPC ....... *A61B 17/0485* (2013.01); *A61B 17/06061* (2013.01); *A61B 17/0487* (2013.01); *A61B 19/26* (2013.01); *A61B 2017/0287* (2013.01); *A61B 2017/0496* (2013.01); *A61B 2019/444* (2013.01)
USPC ............................ 606/148; 606/157; 606/232

(58) Field of Classification Search
USPC ............. 606/1, 144, 148, 151, 157, 158, 232; 600/585; 604/173
See application file for complete search history.

(56) References Cited

U.S. PATENT DOCUMENTS 3,452,740 A    7/1969  Muller
4,102,478 A *  7/1978  Samoilov ........................ 223/99
4,796,626 A    1/1989  DeVries
4,799,496 A    1/1989  Hargreaves et al.
4,829,999 A    5/1989  Auth
4,858,810 A    8/1989  Intlekofer et al.
4,860,742 A    8/1989  Park et al.

(Continued)

FOREIGN PATENT DOCUMENTS

EP            534747        3/1993
WO       WO 01/41860       6/2001

OTHER PUBLICATIONS

Notification of Transmittal of the International Search Report and the Written Opinion of the International Searching Authority issued Dec. 14, 2007 in International Application No. PCT/US2007/06945.

(Continued)

*Primary Examiner* — Elizabeth Houston
*Assistant Examiner* — Todd J Scherbel
(74) *Attorney, Agent, or Firm* — Stoel Rives LLP

(57) ABSTRACT

A surgical securement apparatus for selectively securing one or more ends of a cord while allowing adjustments in the tension or a full release of the cord intermittently after a prolonged period of time. A surgical securement and marking system utilizing one or more surgical securement apparatus that are color-coded to convey information about the associated intercorporeal structures. The surgical securement apparatus can be particularly adapted for use in securing intracorporeal structures such as nerves, blood vessels, and tendons during a surgical procedure. An extender tube connected to the surgical securement apparatus enables securement of intracorporeal structures within the surgical site from outside the surgical site. A threading assembly for use with the surgical securement apparatus that is adapted to facilitate threading of a cord along the length of the surgical securement apparatus.

22 Claims, 8 Drawing Sheets

(56) References Cited

U.S. PATENT DOCUMENTS

| | | | |
|---|---|---|---|
| 4,957,117 A * | 9/1990 | Wysham | 600/585 |
| 4,973,329 A * | 11/1990 | Park et al. | 606/1 |
| 5,137,517 A | 8/1992 | Loney et al. | |
| 5,161,534 A | 11/1992 | Berthiaume | |
| 5,219,332 A | 6/1993 | Nelson et al. | |
| 5,312,338 A | 5/1994 | Nelson et al. | |
| 5,325,746 A | 7/1994 | Anderson | |
| 5,325,868 A * | 7/1994 | Kimmelstiel | 600/585 |
| 5,392,778 A | 2/1995 | Horzewski | |
| 5,423,331 A | 6/1995 | Wysham | |
| 5,634,475 A | 6/1997 | Wolvek | |
| 5,741,301 A | 4/1998 | Pagedas | |
| 5,800,447 A * | 9/1998 | Wenstrom, Jr. | 606/139 |
| 5,851,189 A | 12/1998 | Forber | |
| 5,919,161 A | 7/1999 | Hill, III et al. | |
| 5,987,344 A | 11/1999 | West | |
| 6,015,428 A | 1/2000 | Pagedas | |
| 6,030,349 A | 2/2000 | Wilson et al. | |
| 6,033,414 A | 3/2000 | Tockman et al. | |
| 6,059,484 A | 5/2000 | Greive | |
| 6,171,317 B1 | 1/2001 | Jackson et al. | |
| 6,371,940 B1 | 4/2002 | Valencia et al. | |
| 6,394,976 B1 | 5/2002 | Winston et al. | |
| 6,533,772 B1 | 3/2003 | Sherts et al. | |
| 6,626,917 B1 | 9/2003 | Craig | |
| 6,949,104 B2 | 9/2005 | Griffis et al. | |
| 7,007,060 B2 | 2/2006 | Miller, Jr. | |
| 7,011,635 B1 | 3/2006 | Delay | |
| 7,087,060 B2 | 8/2006 | Clark | |
| 7,144,378 B2 | 12/2006 | Arnott | |
| 7,866,909 B2 | 1/2011 | Denmark | |
| 8,105,355 B2 * | 1/2012 | Page et al. | 606/232 |
| 2001/0031973 A1 | 10/2001 | Nobles et al. | |
| 2003/0225395 A1 | 12/2003 | Griffis et al. | |
| 2003/0229297 A1 | 12/2003 | Christensen et al. | |
| 2004/0067099 A1 * | 4/2004 | Warburton-Pitt | 403/316 |
| 2004/0215108 A1 | 10/2004 | Windheuser | |
| 2005/0070820 A1 | 3/2005 | Boutillette et al. | |
| 2005/0096566 A1 | 5/2005 | Arnott | |
| 2005/0235778 A1 | 10/2005 | Murphy et al. | |
| 2006/0030886 A1 * | 2/2006 | Clark | 606/232 |
| 2007/0106308 A1 * | 5/2007 | Onuki et al. | 606/139 |
| 2007/0142786 A1 * | 6/2007 | Lampropoulos et al. | 604/189 |
| 2007/0219467 A1 * | 9/2007 | Clark et al. | 600/585 |
| 2008/0269785 A1 * | 10/2008 | Lampropoulos et al. | 606/144 |
| 2009/0234295 A1 * | 9/2009 | Lampropoulos et al. | 604/174 |

OTHER PUBLICATIONS

Notification of Transmittal of the International Search Report and the Written Opinion of the International Searching Authority issued Jun. 25, 2009 in International Application No. PCT/US2009/037168.

European Search Report issued May 29, 2009 in co-pending European patent application No. 07753564.9.

Vorwerk, Konner, Schurmann, and Gunther, a Simple Trick to Facilitate Bleeding Control after Percutaneous Hemodialysis Fistula and Graft Interventions, Cardiovasc Intervent Radiol 20 (2) : 159-60 (1997).

Zaleski, Funaki, Gentile, and Garofalo, Purse-string Sutures and Miniature Tourniquet to Achieve Immediate Hemostasis of Percutaneous Grafts and Fistulas: a Simple Trick with a Twist, Am. J. Roentgenol. 175 (6) : 1643-5 (2000).

Simmons, Clark, and Rajan, The Woggle Technique: A New Method of Suture Closure of Hemodialysis Arteriovenous Grafts and Fistulae After Percutaneous Intervention, Journal of Vascular and Interventional Radiology 12(1) :S30 (2001).

Notice of Allowance issued Jan. 10, 2006 in co-pending U.S. Appl. No. 10/198,161.

Response and Amendment filed Oct. 06, 2005 in co-pending U.S. Appl. No. 10/198,161.

Office Action issued Apr. 6, 2005 in co-pending U.S. Appl. No. 10/198,161.

Office Action issued Feb. 7, 2005 in co-pending U.S. Appl. No. 10/198,161.

Preliminary Amendment filed Oct. 6, 2005 in co-pending U.S. Appl. No. 11/244,168.

Office Action issued Feb. 6, 2007 in co-pending U.S. Appl. No. 11/244,168.

Amendment filed Aug. 6, 2007 in co-pending U.S. Appl. No. 11/244,168.

Examiner Interview Summary in co-pending U.S. Appl. No. 11/244,168.

Office Action issued Oct. 18, 2007 in co-pending U.S. Appl. No. 11/244,168.

Notice of Abandonment issued Aug. 7, 2008 in co-pending U.S. Appl. No. 11/244,168.

Office action dated Jun. 11, 2010 in U.S. Appl. No. 11/688,766.

Office action dated Mar. 16, 2010 in U.S. Appl. No. 11/688,766.

Office action dated Oct. 21, 2011 in U.S. Appl. No. 12/404,227.

Office action dated Feb. 15, 2012 in U.S. Appl. No. 12/404,227.

Restriction Requirement dated Jul. 29, 2011 for U.S. Appl. No. 12/404,227.

Restriction Requirement dated Mar. 16, 2010 for U.S. Appl. No. 11/688,766.

Office Action dated Jun. 11, 2010 for U.S. Appl. No. 11/688,766.

Notice of Allowance dated Apr. 28, 2011 for U.S. Appl. No. 11/688,766.

Office Action dated May 20, 2014 for U.S. Appl. No. 12/404,227.

Office Action dated Oct. 15, 2014 for U.S. Appl. No. 12/404,227.

* cited by examiner

SURGICAL SECUREMENT SYSTEM AND APPARATUS

BACKGROUND OF THE INVENTION

1. Field of the Invention

The present disclosure relates to a surgical securement apparatus and a surgical securement and marking system. In more particular, the present disclosure relates to a surgical securement apparatus configured to provide desired gripping of a securement cord which is positioned around one or more intracorporeal structures during a surgical procedure. Additionally, the present invention relates to a securement and marking system configured to facilitate securement, isolation, and identification of intracorporeal structures.

2. Relevant Technology

A variety of surgical procedures require a practitioner to gain access to a patient's thoracic cavity, abdominal cavity or another location within the patient. These procedures often require separating, identifying, and grouping various intracorporeal structures, such as nerves, blood vessels (arteries and veins), and tendons. Sorting the intracorporeal structures allows the practitioner to identify the particular structures to be repaired and to guard against accidental operation on, or damage to, such structures not involved with the procedure. During the course of a surgery, the practitioner may isolate one or more target intracorporeal structures to perform particularized procedures on the structures. A practitioner may also identify various intracorporeal structures that are not being repaired and tie them together or otherwise secure them safely on the periphery of the surgical site. In this manner accidental cutting or otherwise damaging such structures can be avoided.

A variety of techniques have been utilized to secure and at times isolate nerves, vessels, and tendons during a surgical procedure. The techniques generally involve providing a securement loop around the structures to be secured. Typically the securement loop is made of a soft woven tape or cord, such as umbilical tape, that will not inadvertently cut, slice or otherwise damage the structures. Moreover, the techniques can include the use of ties and clamps to secure the securement cord around the structures.

One technique which has traditionally been utilized is simply looping a short section of cord around a target structure and securing the cord utilizing a knot. For description purposes the cord and knot can be referred to as a tie. A significant shortcoming of this technique is the possibility of the tie falling into the surgical area. Blood and fluids in the surgical area can cover or otherwise obscure the tie such that the practitioner may fail to remove the tie at the end of the procedure. Leaving a tie inside a patient after a surgery can cause discomfort, hemorrhaging and increase the possibility of infection. Another significant shortcoming of a simple tie arrangement is that the knot of the tie can be difficult to release once the procedure is over. Leaving the ends of the cord long enough to extend outside the surgical site can help prevent accidental loss of the tie. However, the additional length of cord introduces challenges in initially forming the knot, and the additional length of cord does not help resolve the problems associated with releasing the knot. In light of these shortcomings other techniques have been developed to secure intracorporeal structures during a medical procedure.

Another technique used to secure structures from outside the surgical site employs a section of tubing in connection with a securement cord. The securement cord is threaded in a loop around a target structure. After looping the securement cord around the target structure, the ends of the cord are then threaded through the section of tubing. A distal end of the tubing can be positioned near the structure to enable cinching or tightening of the loop around the structure. A hemostat or clamp can then be placed at the proximal end of the tubing to secure the position of tubing along the loop of cord. The proximal end of the tubing and the hemostat or clamp can remain safely outside the surgical site and the distal end of the section of tubing can hold the loop of securement cord taut around the structure.

The use of this type of securement arrangement utilizing tubing and a hemostat or another clamp, can have several shortcomings. The securement cord loop cannot be pre-threaded through the tubing due to the fact that many of the target structures do not have identifiable or accessible endings around which a pre-formed loop could be threaded. Moreover, quickly and efficiently threading the securement cord through the tubing during the surgical procedure is challenging. For example, introducing one or both ends of the securement cord into a tubing with a small diameter can be complicated and cumbersome. Another shortcoming is that the weight of the hemostat or other clamping device can potentially result in excessive strain on the structures.

BRIEF SUMMARY OF THE INVENTION

Figure 1:
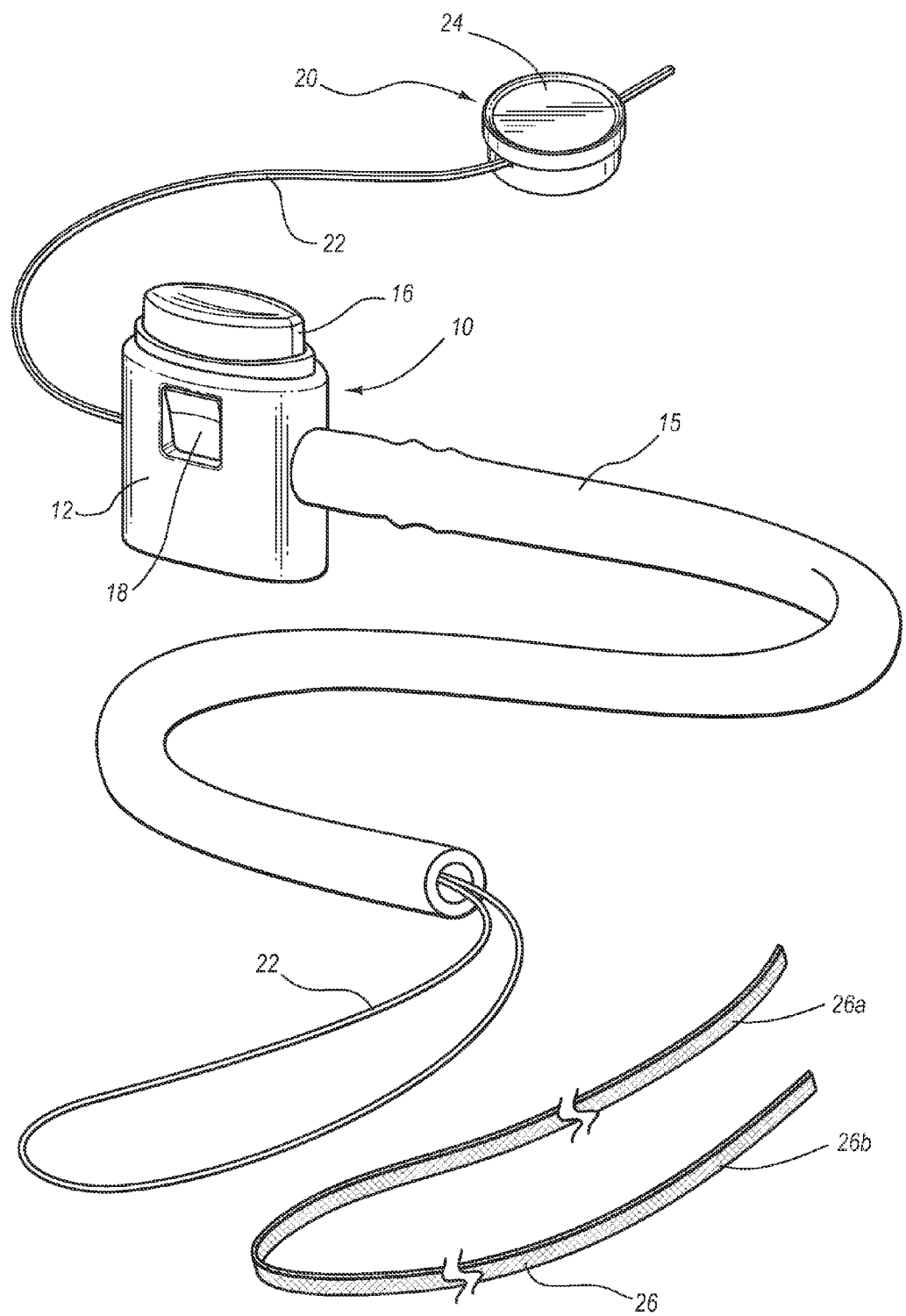
FIG. 1 is a perspective view of a surgical securement apparatus utilized in connection with a threading assembly to secure intracorporeal structures during a surgical procedure.

The present invention relates to a surgical securement apparatus and a surgical securement and marking system utilizing one or more such apparatus. The surgical securement apparatus is configured to selectively secure one or more ends of a cord while allowing adjustments in the tension or a full release of the cord in quick, simple and effective manner. The surgical securement apparatus can be particularly adapted for use with a cord used to sort and secure various intracorporeal structures such as nerves, blood vessels, and tendons during a surgical procedure. The body of the surgical securement apparatus remains outside the surgical site while an extender tube enables securement of structures within the surgical site. The surgical securement apparatus permits a practitioner to subsequently modify the amount of tension or to fully release the cord. The present invention also relates to a threading assembly for use with the surgical securement apparatus that is adapted to facilitate threading of the cord along the length of the surgical securement apparatus. The present invention also relates to a system for marking and securing intracorporeal structures. The system provides an indicator that enables a practitioner to readily identify which intracorporeal structure is associated with a particular securement apparatus. For example, according to one aspect of the present invention, non-textual indicia such as color is provided on the body of a surgical securement apparatus to allow a practitioner to identify the structures associated with that surgical securement apparatus.

According to one embodiment of the present invention, the surgical securement apparatus includes an extender tube which allows tensioning of the cord adjacent to sorted structures while also allowing the body of the surgical securement apparatus to remain outside the surgical site. According to another aspect of the present invention, a threading assembly is provided in connection with the surgical securement apparatus. The threading assembly allows a practitioner to quickly and simply thread one or more tails of the securement cord from the exterior of the surgical securement apparatus and through a lumen of the extender tube and the body of the surgical securement apparatus such that desired engagement of the securement cord is facilitated.

According to one embodiment of the present invention, a clasp and threading loop are provided as part of the threading assembly. The clasp prevents the accidental pulling of the threading loop through the securement apparatus as a result of tension exerted on a portion of the threading loop positioned distal to the securement apparatus. Additionally, the clasp provides a simple and ergonomic mechanism to allow a user to control functioning of the threading assembly and of the threading loop.

According to one embodiment of the present invention, a surgical securement and marking system is provided to enable a practitioner to readily identify various intracorporeal structures. The system includes one or more surgical securement apparatus having integrated non-textual indicia, such as color, to convey to the practitioner information to allow the practitioner to readily identify an associated sorted and secured intracorporeal structure without needing to independently observe or examine the particular structure. Other non-textual indicia that may be integrated with the surgical securement apparatuses include symbols and patterns. The surgical securement system can provide an indication of a particular category, structure name, or other distinguishing characteristic of the structure utilizing indicia on, or the characteristics of, the individual surgical securement apparatus within the system. For example, in one embodiment, a plurality of surgical securement apparatus are provided. Non-textual indicia such as color-coding, is provided on each of the surgical securement apparatus. A practitioner can secure structures utilizing color-coding that allows ready determination that a surgical securement apparatus of a particular color is associated with a particular structure.

DETAILED DESCRIPTION

Surgical procedures accessing the thoracic or abdominal cavity can require separating, sorting, and grouping various intracorporeal structures, including nerves, blood vessels (arteries and veins), and tendons. This process of separating, sorting, and grouping of structures provides the practitioner opportunity to identify the particular target structures to be repaired. The process also separates peripheral structures not involved with the procedure to guard against accidental puncture, incision, or damage of such peripheral structures. The present disclosure enables a practitioner performing a procedure on one or more particular intracorporeal structures, to identify such one or more target structures and separate them from other structures using a securement cord. The practitioner may also identify various intracorporeal structures that are not being repaired and tie them together or otherwise secure them safely on the periphery of the surgical site.

A surgical securement apparatus is provided to selectively secure one or more ends of a securement cord adapted to secure intracorporeal structures. The selective securement of the cord allows adjustments in the tension or a full release of the cord in a simple and effective manner. The body of the surgical securement apparatus provides the securement function. The body can remain outside the surgical site while an extender tube extends into the surgical site to enable securement of intracorporeal structures within the surgical site. This permits a practitioner to adjust the tension or to fully release the cord from outside the surgical site. A threading assembly for use with the surgical securement apparatus is also provided. The threading assembly is adapted to facilitate threading of the cord along the length of the surgical securement apparatus. Also provided is a system which provides an indicator that enables a practitioner to readily identify which intracorporeal structures are associated with a particular surgical securement apparatus. The system can comprise one or more surgical securement apparatus with non-textual indicia such as color integrated thereon. The color or other non-textual indicia convey to a practitioner information about the associated secured intracorporeal structure(s), enabling the practitioner to readily identify associated structure(s). The non-textual indicial allows the practitioner to identify the associated structures without requiring independent observation or examination of the associated structures.

FIG. 1 is a perspective view of a surgical securement apparatus according to one embodiment of the present invention. Surgical securement apparatus 10 is utilized to selectively and releasably secure a securement cord 26 which is adapted to secure intracorporeal structures during various types of surgical procedures. Securement cord 26 is threaded around one or more intracorporeal structures within a surgical site and is then threaded through surgical securement apparatus 10. Surgical securement apparatus 10 facilitates tightening of the loop of securement cord 26 around one or more secured intracorporeal structures. Additionally, surgical securement apparatus 10 is adapted to hang outside the surgical site to enable selective securement of securement cord 26 from outside the surgical site. Selective securement of securement cord 26 allows a practitioner to quickly, easily and intuitively adjust the tension of securement cord 26 around the secured structures or to fully release securement cord 26 at any time. As depicted, surgical securement apparatus 10 comprises a body 12, an extender tube 15, a release button 16, and an assembly window 18.

Body 12 comprises a housing for securing the other components of surgical securement apparatus 10. Body 12 provides desired structure to maintain operability of the components of surgical securement apparatus 10. Body 12 can be colored coded or otherwise labeled to enable a practitioner to quickly identify the intracorporeal structures which are secured by a particular surgical securement apparatus 10. For example, in one illustrative embodiment a practitioner can use a surgical securement apparatus with a red body to secure one or more arteries and to provide a clear indication to the practitioner that the structures secured are arteries. Similarly, a blue body 12 may be utilized as an indicator that one or more veins are being secured. A yellow body 12 may be utilized to indicate nerves, a green body 12 may indicate tendons, and an orange body 12 may indicate the target structure of the procedure.

In another exemplary color-coding scheme, two surgical securement apparatus with a red body 12 can be utilized in a bypass surgery to indicate the blood vessels to be connected during the procedure. As can be appreciated by those skilled in the art, a variety of color-coding schemes can be utilized without departing from the scope and spirit of the present invention. In alternative embodiments, other types of non-textual indicia can be used, including symbols, shapes, and patterns. Moreover, other features such as labels and patterns can be used in connection with body 12 to convey information about the associated intracorporeal structures. Illustrative uses of color-coding and other marking systems in connection with surgical securement apparatus 10 will be discussed in greater detail below with reference to FIG. 6.

In the illustrated embodiment, extender tube 15 is coupled to body 12. Extender tube 15 comprises a resilient tubular member having a lumen formed therethrough. Extender tube 15 can be formed of a flexible material such as flexible PVC, silicone, or other flexible material. Extender tube 15 extends distally from body 12 to access a surgical site. The length of extender tube 15 allows the distal end of extender tube 15 to be positioned within the surgical site and adjacent to intracorporeal structures while body 12 of the surgical securement apparatus remains outside the surgical site. The configuration of extender tube 15 is adapted to facilitate engagement of a securement cord 26 which is utilized during a surgical procedure to secure and/or isolate intercorporeal structures. The securement cord 26 is threaded in a loop or other configuration around one or more intracoporeal structures. The securement cord 26 can then be threaded through the distal end of extender tube 15. The position of extender tube 15 allows surgical securement apparatus 10 to provide a desired degree of tension on the securement cord 26. In this manner, securement cord 26 can be secured from outside the surgical site by surgical securement apparatus 10, thus removing any potential for interference or interruption of the surgical site from body 12 of surgical securement apparatus 10.

Release button 16 is positioned within body 12 of surgical securement apparatus 10. Release button 16 allows a practitioner to selectively secure or release a cord positioned within surgical securement apparatus 10. Selective securement of the cord is accomplished by depressing and releasing release button 16. For example, in the illustrated embodiment when release button 16 is in a released position, surgical securement apparatus securely grips a cord positioned within surgical securement apparatus 10. When the user depresses release button 16, the grip exerted by surgical securement apparatus 10 is loosened, and manipulation of the cord positioned within surgical securement apparatus 10 or adjustment of the surgical securement apparatus 10 relative to the cord can be effectuated. The ability to selectively release and reposition the surgical securement apparatus 10 relative to a cord for which the surgical securement apparatus 10 is to be utilized can be desirable to the extent the practitioner desires to adjust the tension of the cord, reposition the surgical securement apparatus 10 relative to the patient, or perform other desired activities relative to the cord and/or the surgical securement apparatus 10. In particular, at the end of a surgical procedure the practitioner can quickly, simply and efficiently release the cord looped around a secured intracorporeal structures and remove the cord after a given aspect of the procedure is completed or before closing up the surgical site.

Assembly window 18 comprises an aperture in the sidewall of body 12 of surgical securement apparatus 10. Assembly window 18 allows for the quick snap fit assembly of release button 16 relative to body 12 of surgical securement apparatus 10. In the illustrated embodiment, release button 16 includes a biasing flange having a transverse length approximating the width of assembly window 18. During assembly, release button 16 is lowered into body 12 of surgical securement apparatus 10. As release button 16 is urged downward, the biasing flange is received within assembly window 18 preventing inadvertent removal of release button 16 from body 12.

In the illustrated embodiment, surgical securement apparatus 10 is utilized with threading assembly 20. Threading assembly 20 allows a practitioner to quickly and simply thread one or more tails of cord 26 from the exterior of surgical securement apparatus 10 and through a lumen of surgical securement apparatus 10 such that desired engagement of such cord 26 is effectuated. In the illustrated embodiment, threading assembly 20 comprises a threading loop 22 and a clasp 24. Threading loop 22 can comprise a length of nylon suture, or other cord-like material with sufficient strength to pull the tails of cord 26 through the lumen of surgical securement apparatus. Threading loop 22 extends from a proximal portion of surgical securement apparatus 10, along the length of a lumen of body 12 of surgical securement apparatus 10, and extends distally from an end of extender tube 15.

In the illustrated embodiment, clasp 24 includes a first lateral side and second lateral side. Cooperative engagement of the first lateral side and second lateral side secures a portion of threading loop 22 within clasp 24. Clasp 24 secures the end of threading loop 22 positioned on the proximal side of surgical securement apparatus 10. Clasp 24 prevents the accidental pulling of threading loop 22 through surgical securement apparatus 10 as a result of tension exerted on the portion of threading loop 22 positioned distal to surgical securement apparatus 10. Additionally, clasp 24 provides a simple and ergonomic mechanism to allow a user to control functioning of threading assembly 20 and of threading loop 22. According to one embodiment of the present invention, clasp 24 includes texturing or finger grips to allow for desired gripping of clasp 24.

To utilize surgical securement apparatus 10, a user simply threads a first tail 26a and second tail 26b of a securement cord 26 through threading loop 22. Once the first tail 26a and second tail 26b are threaded through threading loop 22, the user grasps clasp 24 and begins to draw threading loop 22 in a proximal direction. As threading loop 22 is retracted in a proximal direction it begins to be drawn into extender tube 15. As threading loop 22 is drawn into extender tube 15, first tail 26a and second tail 26b are also drawn into extender tube 15 thus avoiding the complicated or cumbersome manual introduction of the tips of first tail 26a and second tail 26b into the somewhat small diameter of extender tube 15. A more complete description of the manner in which threading loop 22 draws first tail 26a and second tail 26b of cord 26 into surgical securement apparatus 10 will be described below with reference to FIG. 3.

As will be appreciate by those skilled in the art, a variety of types and configurations of surgical securement apparatus and threading assemblies can be utilized without departing from the scope and spirit of the present invention. According to one embodiment of the present invention, extender tube 15 can be coupled to body 12 via a connector that extends distally from body 12. The connector can further comprise a connector tip adapted to engage and secure extender tube 15 such that the lumen of extender tube 15 is in communication with a lumen of the connector. In another embodiment, extender tube 15 is coupled directly to body 12. In yet another embodiment, extender tube 15 is integrated with body 12. According to another embodiment, an extension mechanism other than an extension tube may be utilized.

According to another embodiment of the present invention, a mechanism to secure a cord other than a depressible button can be utilized. For example, a surgical securement apparatus can comprise a mechanism which has a first locking position to secure the cord and a second unlocked position to release securement of the cord. According to another embodiment, the surgical securement apparatus can be utilized with something other than a securement cord. For example, surgical securement apparatus can be used in conjunction with sutures in a surgical site to selectively secure one or more tails of a suture. A practitioner may use a temporary suture to secure a drainage catheter or other instrument within the surgical site. If the temporary suture must be removed at the end of the procedure, a surgical securement apparatus can be used to selectively secure the suture from outside the surgical site, and thereby prevent it from becoming lost within the surgical site.

Figure 2:
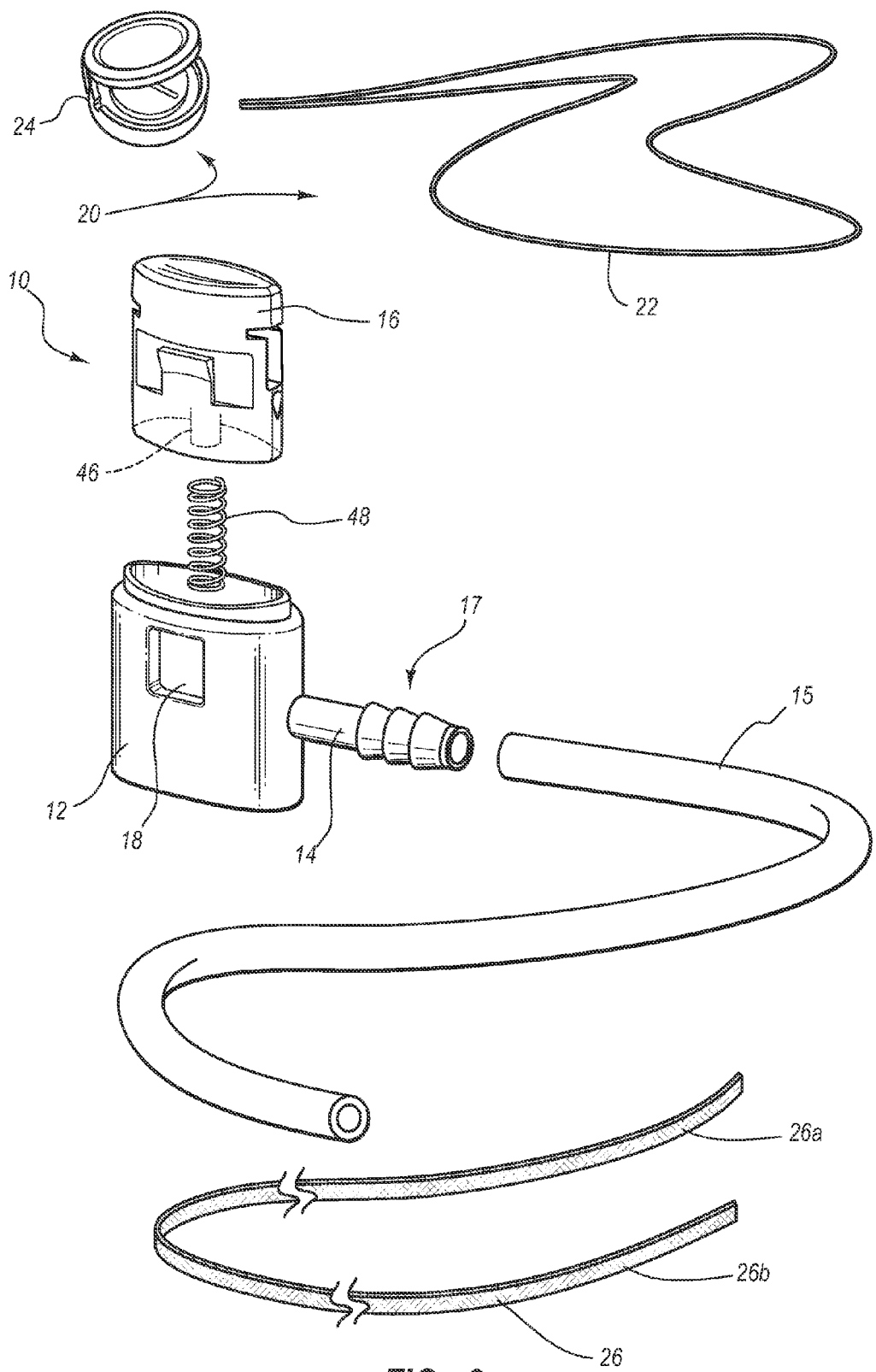
FIG. 2 is an exploded view of a surgical securement apparatus.

FIG. 2 is an exploded view of a surgical securement apparatus. As discussed with reference to FIG. 1, surgical securement apparatus 10 comprises a body 12, a flexible extender tube 15, a release button 16, and an assembly window 18. Threading loop 22 or sorting cord 26 can be threaded through surgical securement apparatus 10 by extending threading loop 22 through a lumen of body 12, a lumen of release button 16, and a lumen of extender tube 15.

In the illustrated embodiment, a connector 14 of surgical securement apparatus 10 is depicted. Connector 14 is secured to body 12 of surgical securement apparatus such that it that extends distally from body 12. Connector 14 provides a mechanism to connect body 12 to extender tube 15. Connector 14 comprises a lumen that integrates with and/or forms a portion of a lumen through surgical securement apparatus 10. According to one aspect, connector 14 has a tapered mouth, such that there is a smooth transition from the lumen of connector 14 to the lumen of extender tube 15. A tapered mouth facilitates threading of securement cord 26 through the lumen of surgical securement apparatus 10 by guiding first tail 26a and second tail 26b into the lumen of body 12. The tapered mouth of connector also minimizes snagging or interference with proper operation of surgical securement apparatus 10 as a practioner retracts threading loop 22 and/or tightens securement cord 26 during use of surgical securement apparatus 10.

Connector 14 can further comprise a connector tip 17 that is configured to engage and secure extender tube 15. In the illustrated embodiment, connector tip 17 can include a barbed connector, such as a "Christmas tree" type connector. Connector tip 17 can comprise a plurality of tapered ramps, or barbs. The tapered ramps have a smaller cross-section at their distal end and increase in thickness as each ramp approaches its proximal most extent. The ramps are adapted to allow extender tube 15 to slide onto connector 14. The ramps then engage the interior of extender tube 15 and thereby restrict extender tube 15 from sliding in the opposite or distal direction such that the tube would be removed from connector 14. Connector tip 17 engages extender tube 15 in a manner that allows the lumen of extender tube 15 to be in communication with the lumen of connector 14, thus allowing a continuous lumen through both structures, as discussed more fully below with reference to FIG. 3A.

In the illustrated embodiment, release button 16 is adapted to be positioned within body 12. A biasing member 48 fits within body 12 in abutment with release button 16. The biasing member 48 can comprise a spring. The biasing member is adapted to be positioned around or adjacent to a post 46 of release button 16. Post 46 is positioned on the underside of release button 16 such that it is located within body 12 and in abutment with, and/or adjacent to, biasing member 48. Biasing member 48 exerts a biasing force urging release button 16 in an upward direction. As release button 16 is urged in an upward direction, a cord threaded through surgical securement apparatus 10 is secured by release button 16. A more complete description of the manner in which surgical securement apparatus 10 engages and secures a cord will be described below with reference to FIG. 3A.

As will be appreciated by those skilled in the art, a variety of types and configurations of surgical securement apparatus can be utilized without departing from the scope and spirit invention. For example, in one embodiment, the surgical securement apparatus is provided without a threading assembly. According to yet another embodiment, a connector other than a barbed "Christmas tree" connector can be utilized to secure an extender tube to a connector. For example, the connector may comprise a clip, a fastener, or a detent. In yet another embodiment, the connector tip includes ribs instead of barbs. In still another embodiment, no connector tip is employed, but rather the shape of the connector and/or a friction fit provided between the connector and the extender tube secures the extender tube relative to the body of the surgical securement apparatus.

Figure 3A:
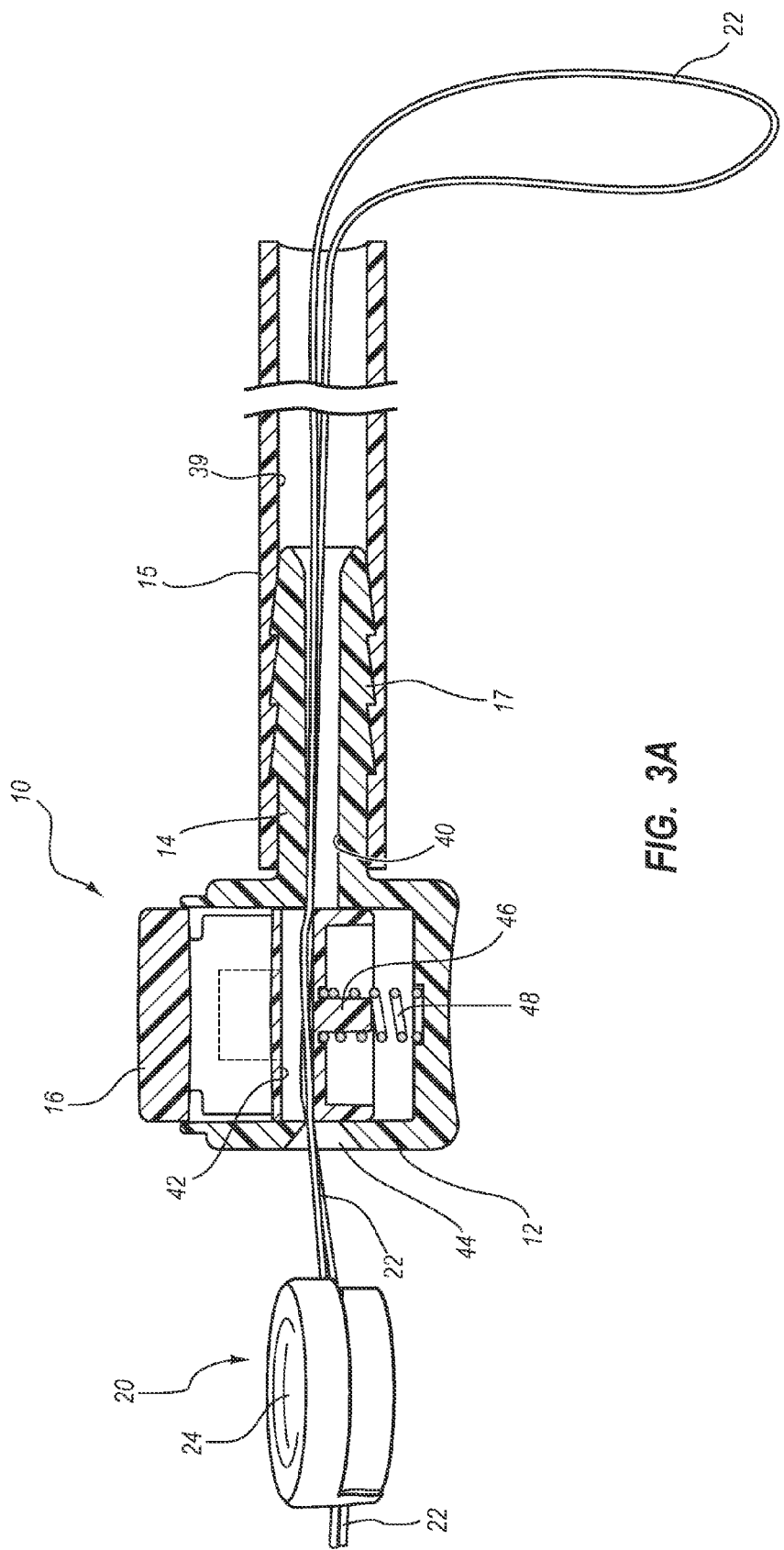
FIG. 3A is a cross-sectional side view of a surgical securement apparatus illustrating a threading assembly positioned within the surgical securement apparatus.

FIG. 3A is a cross-sectional side view of surgical securement apparatus 10 according to one embodiment of the present invention. In the illustrated embodiment, a connector 14 includes a barbed connector tip 17 that engages and secures extender tube 15 relative to the other components of surgical securement apparatus 10. In the illustrated embodiment, barbed connector tip 17 comprises a "Christmas tree" connector. The barbs of connector tip 17 are adapted to allow extender tube 15 to slide onto connector 14. Once the extender tube 15 slides past a barb, the barb engages the inside of the extender tube and thereby restricts extender tube 15 from sliding in an opposite direction such that it is removed from connector 14. Barbed connector tip 17 engages and secures extender tube 15 in a manner that lumen 39 of extender tube 15 is in communication with lumen 40 of connector 14. The connector lumen 40 runs through the center of connector tip 17. Connector tip 17 is inserted and received into extender tube lumen 39, thus allowing a continuous lumen through both structures.

The cross-sectional view of FIG. 3A also illustrates that lumen 40 of connector 14 can have a tapered distal aperture to facilitate threading of securement cord 26 through surgical securement apparatus 10. Tapering of the distal aperture provides a larger opening to receive the threaded first tail 26a and second tail 26b of securement cord 26. Tapering also reduces the surface area of connector tip 17 at the interface of lumen 39 of extender tube 15 and lumen 40 of connector 14. The tapered distal aperture thus minimizes the possibility that cord 26 could get snagged while being pulled through surgical securement apparatus 10 by threading assembly 20.

FIG. 3A further depicts a rear aperture 44. Rear aperture 44 receives threading loop 22 as it is inserted into surgical securement apparatus 10. The tails of a securement cord 26 extend proximally from rear aperture 44 once cord 26 has been threaded through surgical securement apparatus 10. In the illustrated embodiment, rear aperture 44 is positioned in substantial alignment with connector lumen 40. Rear aperture 44 has a tapered configuration which facilitates the loading of threading loop 22 into surgical securement apparatus 10.

According to one alternative embodiment of the present invention, a tapered extension tube is provided in place of or in addition to a rear aperture 44.

In the illustrated embodiment, release button 16 is depicted in an undepressed position. Threading loop 22 extends through surgical securement apparatus 10 such that a portion of threading loop 22 projects distally from extender tube 15. The portion of threading loop 22 which extends distally of extender tube 15 is utilized to capture a securement cord and thread the securement cord through surgical securement apparatus 10.

In the illustrated embodiment, when release button 16 is in an undepressed position, threading loop 22 is engaged between release button 16 and body 12 restricting movement of threading loop 22 relative to surgical securement apparatus 10. Spring member 48 is positioned adjacent post 46 such that spring member 48 exerts a biasing force on post 46 to urge release button 16 in an upward direction. When release button 16 is urged to its upward most displacement relative to body 12, release button lumen 42 is placed slightly out of alignment with connector lumen 40. In this manner threading loop 22, or anything threaded through the lumen of surgical securement apparatus, is compressed between the bottom surface of release button lumen 42 and both the top of connector lumen 40 and the top surface of rear aperture 44. The cooperative engagement of the surfaces of connector lumen 40, release button 42, and rear aperture 44 provide an effective mechanism for securing a desired degree of tension on threading loop or another cord threaded along the length of surgical securement apparatus 10.

Figure 3B:
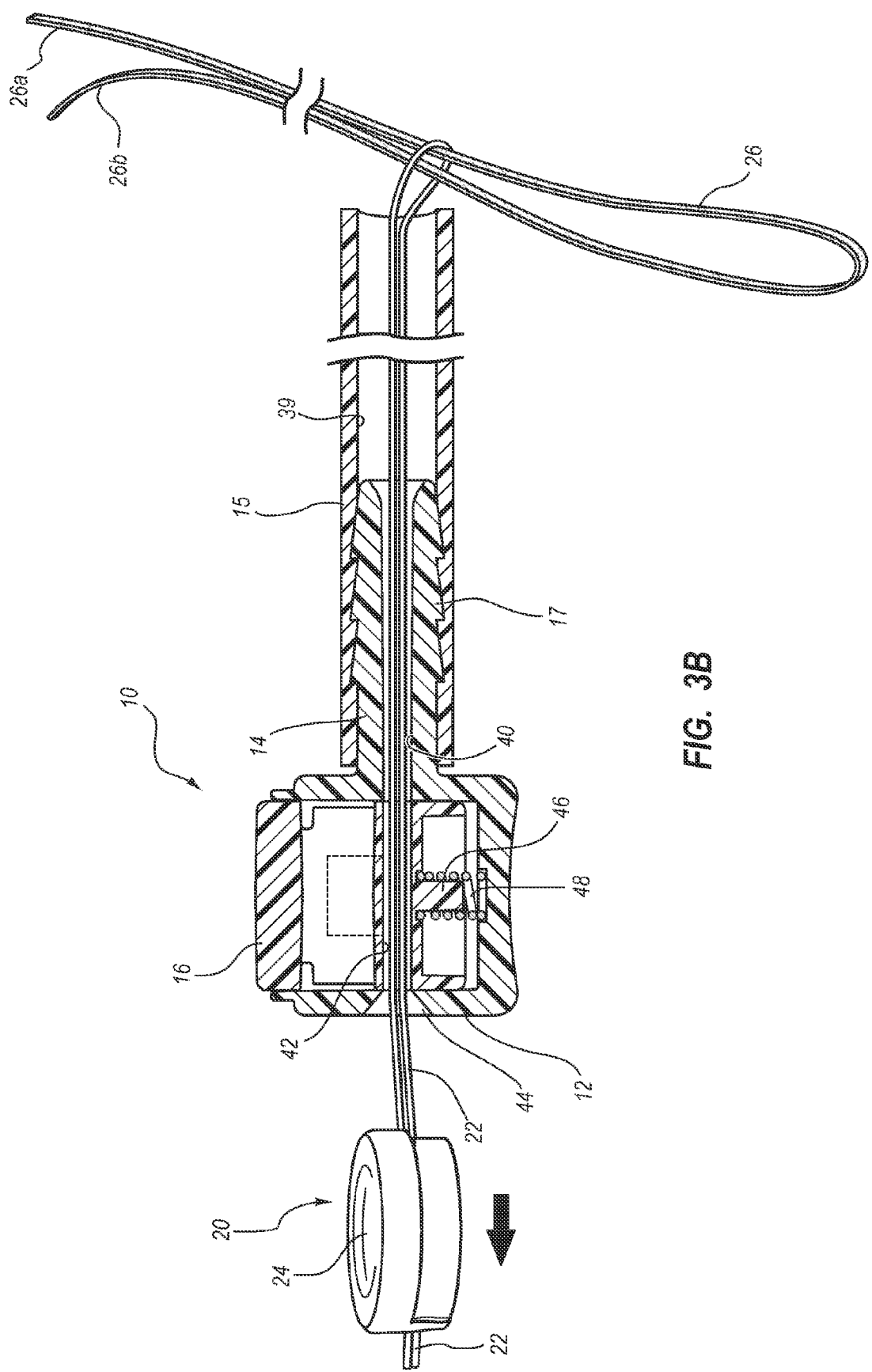
FIG. 3B is a cross-sectional side view of a surgical securement apparatus in which the release button is depressed and threading assembly is being utilized engage a securement cord.

FIG. 3B depicts release button 16 in a depressed position. The practitioner depresses release button 16 when loosening the tension is desired. As the practitioner depresses release button 16, the release button 16 is urged in a downward direction and spring member 48 is depressed. Additionally, as release button 16 is urged in a downward direction, release button lumen 42 aligns with connector lumen 40 and rear aperture 44. As a result, threading loop 22 is no longer cooperatively engaged between opposing surfaces of release button lumen 42, connector lumen 40, and rear aperture 44. When threading loop 22 is not cooperatively engaged, the securement on threading loop 22 is released and threading loop 22 is moveable with respect to surgical securement apparatus 10.

When the release button 16 is depressed and the threading loop 22 is released, clasp 24 can be retracted in a rearward direction to pull threading loop 22 in a proximal direction. In the illustrated embodiment, first tail 26a and second tail 26b are threaded through threading loop 22. As clasp 24 is retracted in a rearward direction, the portion of threading loop 22 projecting distally from extender tube 15 is drawn into an extender tube lumen 39. Because first tail 26a and second tail 26b are threaded through threading loop 22, retraction of threading loop 22 pulls first tail 26a and second tail 26b into extender tube lumen 39. As clasp 24 is further retracted in a rearward direction, threading loop 22 is drawn into a connector lumen 40 of connector 14. Accordingly, first tail 26a and second tail 26b are also pulled into connector lumen 40. The distal end of connector 14 may be tapered, as depicted, to thereby facilitate guidance of first tail 26a and second tail 26b into connector lumen 40.

Figure 3C:
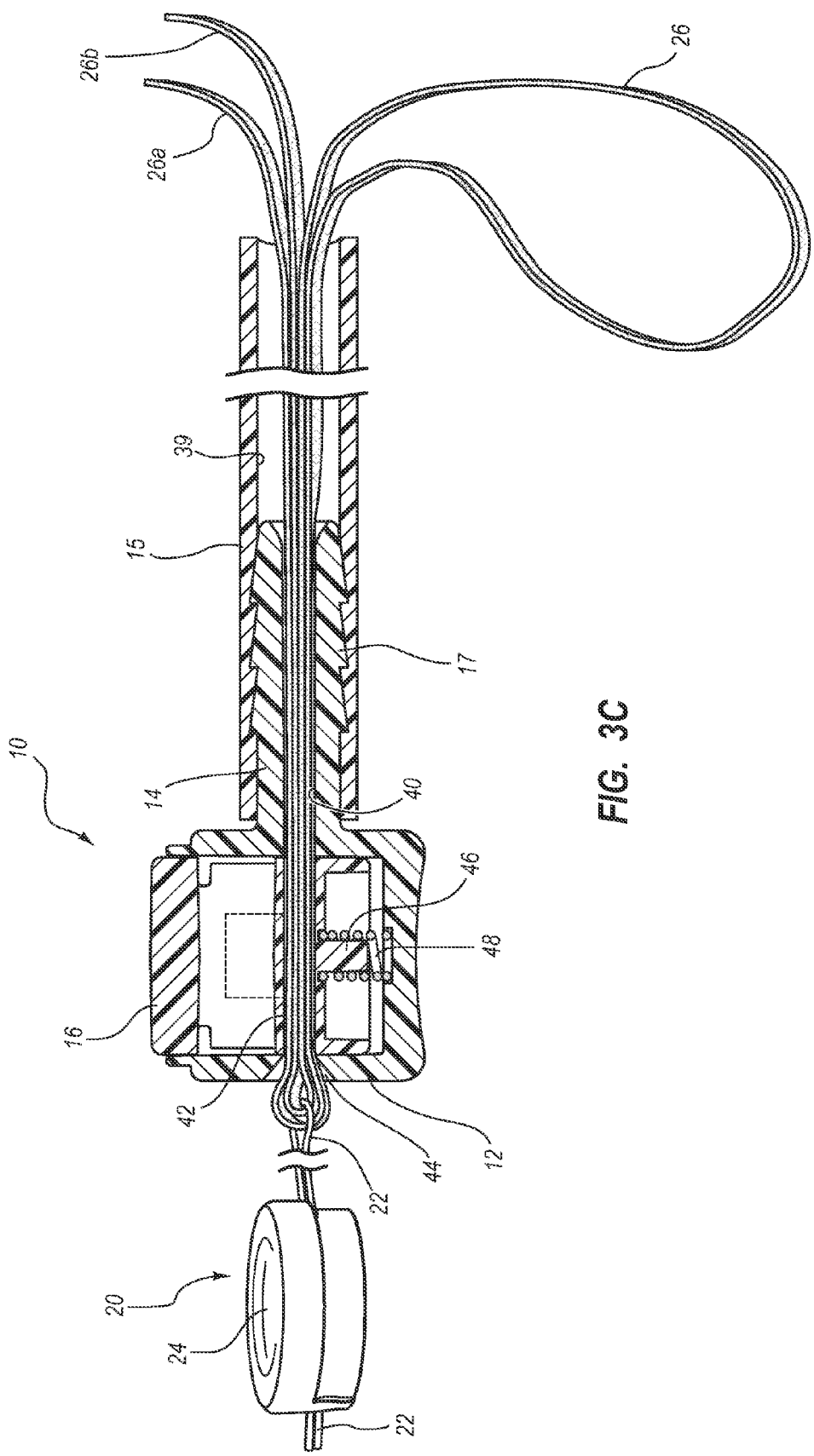
FIG. 3C is a cross-sectional side view of a surgical securement apparatus in which the securement cord is being threaded through the surgical securement apparatus.
Figure 5:
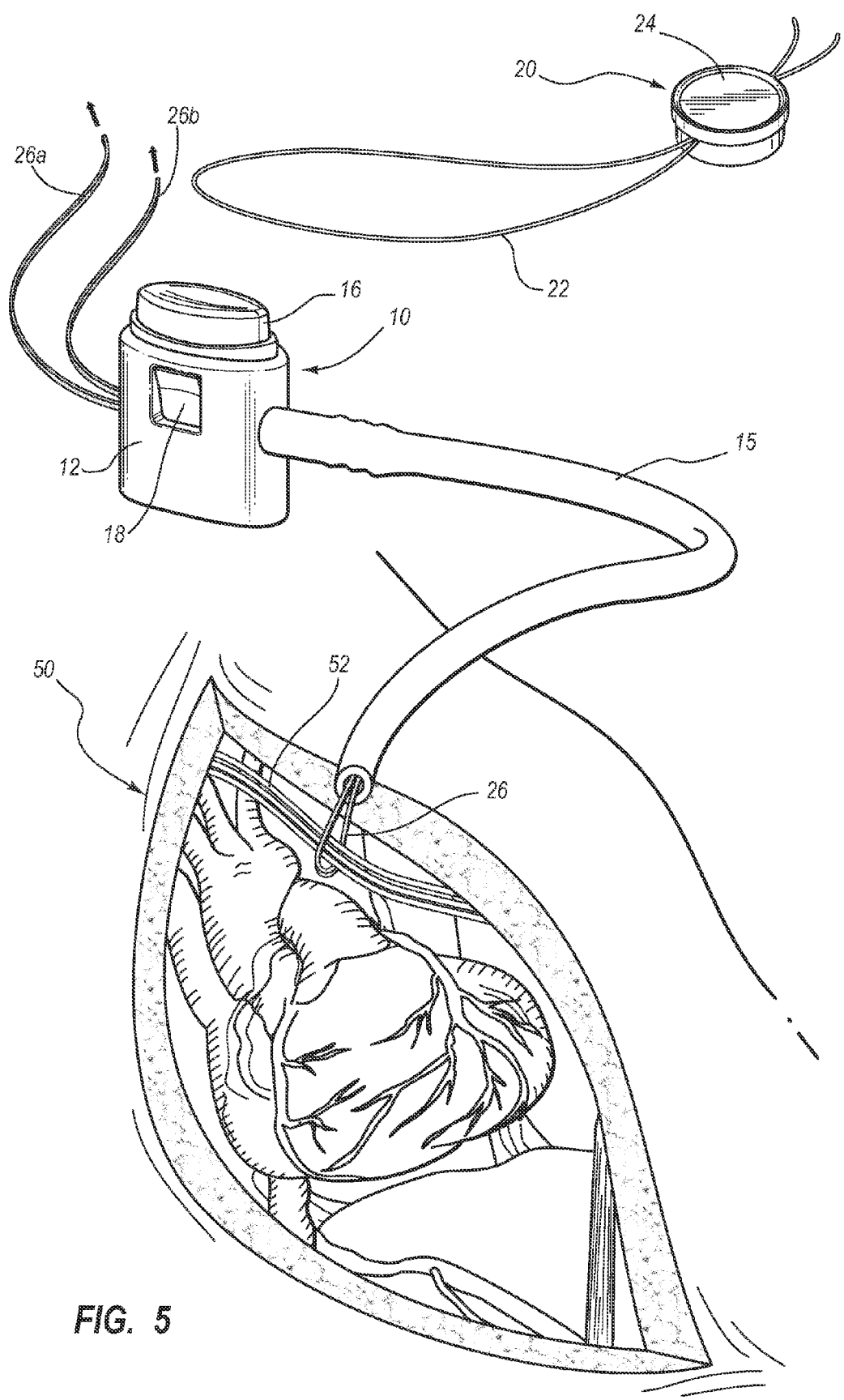
FIG. 5 is a perspective view of a surgical securement apparatus positioned to secure a securement cord with a desired degree of tension around a structure to be secured during a surgical procedure.

FIG. 3C illustrates the manner in which clasp 24 and threading loop 22 are utilized to draw securement cord 26 into surgical securement apparatus 10. In the illustrated embodiment, release button 16 is in a depressed position similar to the position of release button 16 in FIG. 3B. When release button 16 is in a depressed position, release button lumen 42 aligns with connector lumen 40 and rear aperture 44. As threading loop 22 is pulled in rearward direction, first tail 26a and second tail 26b are also drawn into release button lumen 42. As will be appreciated by those skilled in the art, as the practitioner continues to retract threading assembly 20 in a rearward direction, first tail 26a and second tail 26b are pulled along the entire length of surgical securement apparatus 10 until first tail 26a and second tail 26b extend out of a rear aperture 44 of surgical securement apparatus 10, as depicted in FIG. 5. In this manner, threading assembly 20 facilitates the quick, simple and intuitive threading of first tail 26a and second tail 26b of securement cord 26 through surgical securement apparatus 10.

Once securement cord 26 is completely threaded through surgical securement apparatus 10, a practitioner may desire to secure the position of securement cord 26 within securement apparatus 10. To secure securement cord, the practitioner simply allows button 10 to be released to an undepressed position. As described above with reference to FIG. 3A, release button 16 engages securement cord 26 when release button 16 is in an undepressed position. Release button 26 engages securement cord 26 by compressing securement cord 26 between the bottom surface of release button lumen 42 and both the top of connector lumen 40 and the top surface of rear aperture 44. Thus, release button 16 provides selective securement of securement cord 26.

The practitioner can also release engagement of securement cord 26 by depressing release button 16. As described above with reference to FIG. 3B, as release button 16 is urged in a downward direction, release button lumen 42 becomes aligned with connector lumen 40 and rear aperture 44. Securement cord 26 is no longer cooperatively engaged between opposing surfaces of release button lumen 42, connector lumen 40, and rear aperture 44. Accordingly, the practitioner can move surgical securement apparatus 10 laterally relative to first tail 26a and second tail 26b. Releasing of the securement of securement cord 26 by depression of release button 16 allows the practitioner to loosen, tighten, or make other changes in the juxtaposition of surgical securement apparatus 10 relative to securement cord 26 and the one or more intracorporeal structures thereby secured.

As will be appreciated by those skilled in the art, a variety of types and configurations of surgical securement apparatus can be utilized without departing from the scope and spirit invention. For example, the juxtaposition and mechanisms utilized to secure a cord relative to the surgical securement apparatus can vary without departing from the scope and spirit of the present invention. For example, a cord which is threaded through the release button may be cooperatively engaged by surfaces other than the bottom surface of the release button and the top of the connector lumen and top of the rear aperture. Additionally, the lumen of the release button may vary in size. A top surface of the lumen may remain fixed, while the bottom surface of the lumen clamps against the top surface as the release button is depressed. The top and bottom surfaces of the release button lumen and other lumens can further comprise one or more protrusions or other non-slip surfaces to facilitate desired engagement of a cord. In one embodiment, the top and bottom surfaces of the lumen can include grooves which receive protrusions from the opposite surface thereby enhancing engagement of the cord by the protrusions.

Figure 4:
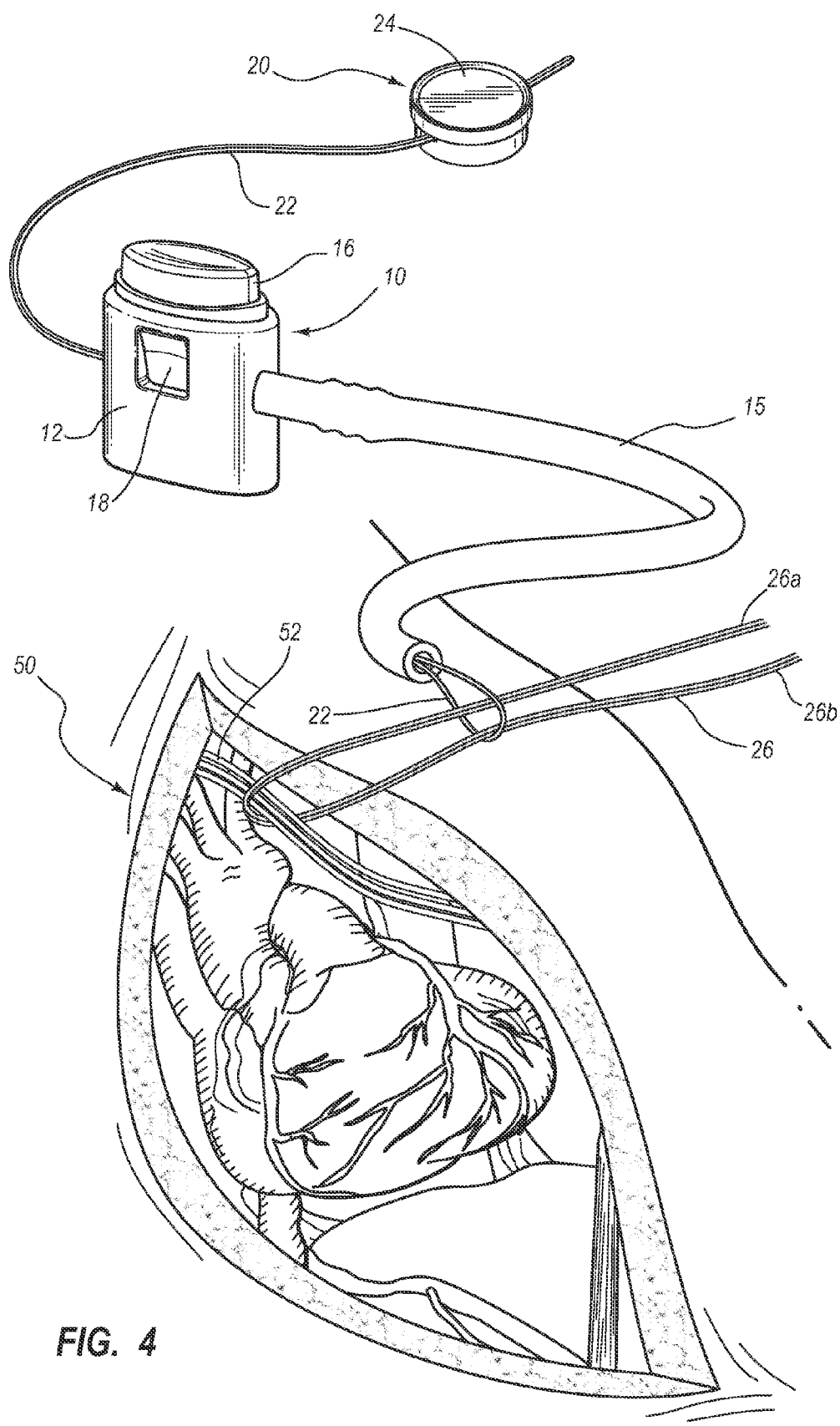
FIG. 4 is a perspective view of a surgical securement apparatus being utilized in connection with a surgical procedure.

FIG. 4 is a perspective view of a surgical securement apparatus 10 being utilized in connection with a surgical procedure. In the illustrated embodiment, securement cord 26 is threaded around one or more intracorporeal structures 52 within a surgical site 50. First tail 26a and second tail 26b of securement cord 26 have been threaded through threading loop 22. Threading assembly 20 is partially retracted, such that threading loop 22 has been advanced adjacent to the tip of extender tube 15. As threading loop 22 is further retracted, threading loop 22 will draw first tail 26a and second tail 26b into the lumen of extender tube 15.

Securement cord 26 facilitates desired securement of intracorporeal structures 52 within the patient. In the illustrated embodiment, the depicted surgical environment is an open heart surgery. The surgical site 50 is opened exposing a variety of intracorporeal structures including the heart, various vessels and intracorporeal structures 52. As will be appreciated by those skilled in the art, intracorporeal structures 52 are representative of any of plurality of different intracorporeal structures that may need to be secured during a surgical procedure. Securement cord 26 is threaded around intracorporeal structures 52 allowing a practitioner to hold, secure, manipulate or even draw intracorporeal structures 52 from surgical site 50 utilizing securement cord 26.

First tail 26a and second tail 26b have been threaded through threading loop 22. The design of threading loop 22 and threading assembly 20 allows the practitioner to simply and easily draw first tail 26a and second tail 26b through threading loop 22. For example, in the even that a larger diameter of threading loop 22 positioned distal to extension tube 15 is needed, the practitioner can simply advance threading loop 22 in a distal direction. To advance threading loop 22, the user simply depresses release button 16, and advances clasp 24 in the direction of surgical securement apparatus 10. By advancing clasp 24 in the direction of surgical securement apparatus 10, the suture material comprising threading loop 22 is also advanced such that a greater portion of threading loop 22 is positioned distal to the tip of extender tube 15. In this manner, a larger threading loop 22 is provided facilitating a straightforward threading of first tail 26a and second tail 26b through threading loop 22. Once first tail 26a and second tail 26b have been threaded through threading loop 22, a user can simply draw securement cord 26 adjacent the tip of extender tube by retracting clasp 24 away from threading assembly 20.

FIG. 5 is a perspective view of a surgical securement apparatus 10 in which securement cord 26 has been threaded through surgical securement apparatus 10. In the illustrated embodiment, securement cord 26 is positioned around various intracorporeal structures 52 to be secured during a surgical procedure. Threading assembly 20 has been fully retracted, such that threading loop 22 is withdrawn from surgical securement apparatus 10. Accordingly, first tail 26a and second tail 26b of securement cord 26 have been threaded along the entire length of surgical securement apparatus, through extender tube 15, connector 14, and body 12, such that first tail 26a and second tail 26b are extending from rear aperture 44 (See also FIGS. 3A-3C). Surgical securement apparatus 10 and extender tube 15 of surgical securement apparatus 10, have been advanced forward along securement cord 26 such that the distal end of extender tube 15 is positioned adjacent intracorporeal structures 52 and the loop in securement cord 26 can be held taut. Although the figure depicts the securement cord 26 as being somewhat loose, it can be appreciated by those skilled in the art that the tension of the securement cord can be adjusted as desired.

Extender tube 15 enables securement of intracorporeal structures 52 within surgical site 50 while allowing the body of surgical securement apparatus 10 to remain outside surgical site 50. Extender tube 15 provides displacement between the tip of extender tube 15 and body 12 of surgery securement apparatus. The length of extender tube 15 can be selected to ensure that the body of surgical securement apparatus 10 remains outside surgical site 50 while the distal tip of extender tube 15 can be placed immediately adjacent one or more intracorporeal structures 52. The displacement from the distal tip of extender tube and body 12 allows desired securement at the tip of extender tube 15 while providing actuation of button 16 at a desired displacement from surgical site 50.

Body 12 can be positioned outside of surgical site 50, so as to not obstruct any structures or otherwise impede the surgical procedure. According to one aspect of the invention, surgical securement apparatus 10 is configured to hang outside of surgical site 50 such that body 12 can provide an appropriate amount of weight to stabilize and/or draw ancillary structures to the periphery of surgical site 54. Additionally, the position of body 12 makes body 12 and button 16 readily accessible for a practitioner in the event that a practitioner desires to manipulate a desired structure to which surgical securement apparatus 10 is secured.

In the illustrated embodiment, body 12 of surgical securement apparatus 10 can be colored to provide an indication of the type of intracorporeal structures 52 being secured with the corresponding securement cord 26. For example, body 12 of surgical securement apparatus 10 can be colored blue. Color coding or other sorting indicia allow the practitioner to sort and secure veins. Additionally, the particular color or other sorting indicia can be utilized to communicates to a practitioner the type of structures being secured. In one illustrative embodiment, the color blue can indicate to the practitioner that the secured structures are veins.

Figure 6:
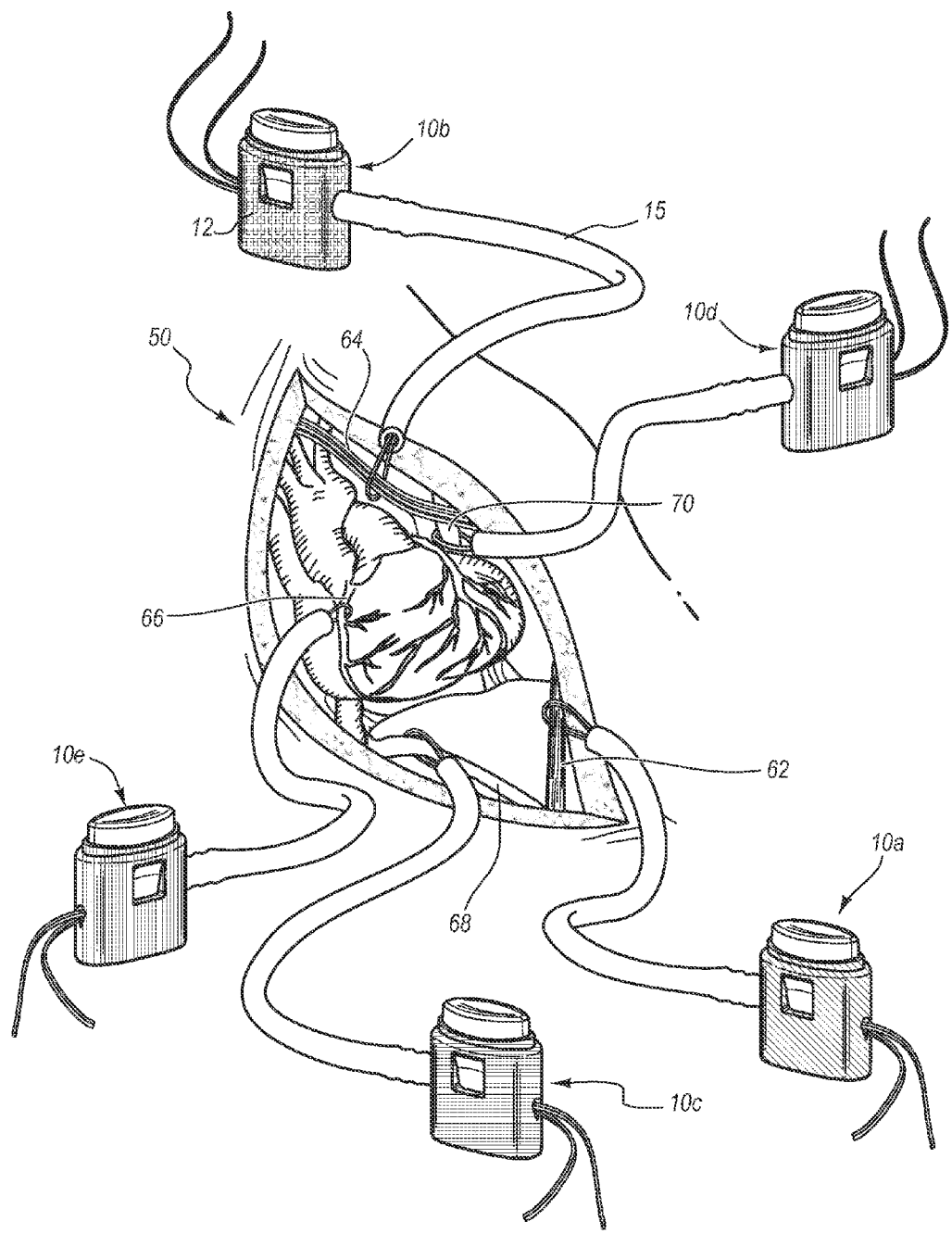
FIG. 6 is a perspective view of a surgical securement and marking system employing color-coded surgical securement apparatus to sort and secure various intracorporeal structures during a surgical procedure.

FIG. 6 illustrates an exemplary embodiment of an surgical securement and marking system employing multiple color-coded surgical securement apparatuses to secure and mark various intracorporeal structures within a surgical site 50 of coronary bypass surgery. The surgical securement apparatuses are color-coded to aid practitioners in identifying the intracorporeal structures which are secured by surgical securement apparatus 10a-10e. The color-coding provides an indication of the associated structure so that the practitioner does not need to independently examine the structure to identify it again after the structure is secured. Other non-textual indicia may be utilized in connection with the color-coding, or in alternative to the color-coding, such as symbols and patterns.

In the illustrated embodiment, surgical securement apparatus 10a is colored green indicating that the corresponding sorted and secured intracorporeal structure is a tendon 62. Surgical securement apparatus 10b is colored yellow indicating that the corresponding sorted and secured intracorporeal structure is a nerve 64. Surgical securement apparatus 10c is colored blue indicating that the corresponding structure is a vein 66. Surgical securement apparatuses 10d and 10e are colored red indicating that the corresponding structures are arteries 68, 70.

The color coded system can be adapted for various purposes and procedures. For examples, surgical securement apparatuses of like color can be used to associate various intracorporeal structures in ways other than structure type. For example, surgical securement apparatuses 10d and 10e can both be colored red to indicate that the structures secured by each are to be connected together during a procedure such as coronary bypass. In one method of performing coronary bypass surgery, the mammary artery is severed and connected to the coronary artery below the blockage, thereby providing oxygen-rich blood to the heart tissue below the blockage. Surgical securement apparatuses that are color-coded with like colors can be used to sort and secure the mammary artery and the coronary artery. For example, surgical securement apparatus 10d may secure the mammary artery 68 while surgical securement apparatus 10e may secure the blocked coronary artery 70 to be bypassed. The practitioner is thereby aided in avoiding operating on an incorrect blood vessel, and can quickly identify the connection that needs to be made to complete the bypass.

In another method of performing coronary bypass surgery, a blood vessel, usually a harvested vein from another part of the patient's body, is connected to the aortic artery at one end, and then to the blocked coronary artery at a position below the blockage, thereby supplying the tissue below the blockage with a supply of oxygen rich blood. The ends of the harvested blood vessels, the aorta, and the coronary artery to be bypassed can be sorted and secured by various securement cords and surgical securement apparatus. The surgical securement apparatuses can be color coded to provide easy identification of the various parts to be connected by the procedure. For example, the aorta and one end of the harvested vessel may each be secured by surgical securement apparatuses having the same color. Similarly, the other end of the harvested vessel and the coronary artery may each be secured by like colored surgical securement apparatuses having a color different than the other surgical securement apparatus. In this manner, the practitioner can easily identify the vessels to be connected in the surgery.

In another embodiment of a surgical securement and marking system, colors and other non-textual indicia may indicate the structures associated with the steps of a surgical procedure. For example, a practitioner may secure and mark one or more intracorporeal structures involved in a first step of the procedure with a particular color. Similarly, the one or more structures of a second step may be marked with another color, and so on. In another embodiment, surgical securement apparatus colored similarly may be used to secure and mark ancillary structures that are not involved in the procedure. For example, gray surgical securement apparatus may indicate the associated structures are not being treated during the procedure and can be moved to the periphery of the surgical site or otherwise ignored by the practitioner.

Other types of non-textual indicia can also be utilized for marking. Examples of other non-textual indicia include symbols and patterns. Particular symbols may be placed on body 12 of surgical securement apparatus to quickly convey information to practitioners. For example, in FIG. 6, a star or other symbol may be integrated on both surgical securement apparatus 10d and surgical securement apparatus 10e. The practitioner can readily recognize that the structures secured by surgical securement apparatus having like symbols, such as stars, are associated. In the case of bypass surgery, the association can be that the structures that are to be connected during the procedure. The symbols can also be colored to provide additional information. Patterns can be used in a similar manner. For example, a red body 12 of a surgical securement apparatus 10d may further comprise a pattern such as three parallel lines or stripes. The practitioner can readily recognize an association of intracorporeal structures secured by such apparatus with structures secured by an apparatus having the same or corresponding pattern. Moreover, other features such as labels can be included on body 12 to convey additional information about the associated intracorporeal structures.

As will be understood by those skilled in the art, utilization of the surgical securement apparatus with a securement cord to secure intracorporeal structures is merely an exemplary embodiment illustrating operation of the surgical securement apparatus relative to securing such intracorporeal structure and should in no means be considered to be limiting in nature. For example, the surgical securement apparatus can be utilized with sutures that are positioned within the surgical site. Additionally, the surgical securement apparatus can be utilized for securing additional medical devices such as a suture ring of a catheter hub to a patient. Moreover, the color-coding examples disclosed are merely exemplary illustrations and should in no means be considered to be limiting in nature. For example, symbols, patterns, texturing or other indicia can be utilized with a sorting and securement system. A desired securement and sorting system can be adapted for particularized procedures, medical specialities, medical facilities, or even individual surgical teams, and available colors can be adapted in a variety of ways to conform to any particular color-coding scheme.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A surgical securement assembly for securing one or more intracorporeal structures during a surgical procedure, the surgical securement assembly comprising:
   a securement cord configured to extend around one or more intracorporeal structures;
   a surgical securement apparatus, comprising:
      a body having a cavity positioned therein;
      a plunger comprising a plunger lumen, the plunger slidably disposed within the cavity of the body;
      a biasing spring positioned within the cavity of the body and engaging the plunger to bias the plunger and allow for releasable engagement of the securement cord;
      a connector extending outwardly from the body; and
      an extender tube coupled to the connector, the extender tube extending between a proximal end directly coupled to the connector and a distal end, the distal end distally offset from the connector,
      wherein the distal end of the extender tube is disposable adjacent one or more intracorporeal structures and the body is disposable at a predetermined displacement from the distal end of the extender tube such that the body can remain outside the surgical site when the distal end of the extender tube is within the surgical site;
      and wherein the extender tube is configured to accommodate a portion of the securement cord therein such that the distal end of the extender tube draws opposite portions of the securement cord together to form a loop of the securement cord, such that the extender tube closes the loop and provides tension on the loop at a location adjacent an intracorporeal structure;
      and wherein the extender tube is flexible along its length such that the body is displaceable outside the surgical site while the distal end of the extender tube remains adjacent an intracorporeal structure and such that a location wherein the extender tube closes the loop and provides tension on the loop is flexibly offset from a location wherein the plunger engages the securement cord; and
   a threading assembly having a base and a threading loop comprising a suture material for facilitating threading of the securement cord through each of a connector lumen, a lumen of the surgical securement apparatus, and the plunger lumen, wherein the base engages tails of the threading loop adjacent free ends of the threading loop tails, and wherein each of the connector lumen, the lumen of the surgical securement apparatus, and the plunger lumen comprises dimensions sufficient for passage of both the threading loop and the securement cord when the securement cord is threaded through the threading loop and folded over.

2. The surgical securement apparatus of claim 1, wherein the intracorporeal structures secured by the securement cord are selected from the group consisting of nerves, arteries, veins, tendons and muscles.

3. The surgical securement apparatus of claim 1, wherein the body of the surgical securement apparatus includes one or more non-textual indicia conveying information about the one or more intracorporeal structures secured by the apparatus.

4. The surgical securement apparatus of claim 3, wherein the one or more non-textual indicia comprise colors.

5. The surgical securement apparatus of claim 3, wherein the one or more non-textual indicia comprise symbols.

6. The surgical securement apparatus of claim 3, wherein the one or more non-textual indicia comprise a pattern.

7. The surgical securement apparatus of claim 1, wherein the plunger comprises a release button.

8. The surgical securement apparatus of claim 1, wherein the securement cord positioned through the connector lumen and plunger lumen of the surgical securement apparatus can be moved relative to the securement apparatus when the connector lumen and the plunger lumen are aligned, and wherein the securement cord is secured relative to the securement apparatus when the connector lumen and the plunger lumen are not aligned.

9. The surgical securement apparatus of claim 1, wherein the connector is integrally coupled to the body of the securement apparatus.

10. The surgical securement apparatus of claim 1, wherein the connector is a barbed connector comprising a connector lumen and one or more barbs on an exterior surface of the barbed connector, such that the barbed connector is configured to engage and secure the extender tube to the connector in a manner that a lumen of the extender tube is in communication with the connector lumen.

11. The surgical securement apparatus of claim 10, wherein the barbed connector is a Christmas-tree type connector.

12. A method of utilizing a surgical securement assembly, the method comprising:

obtaining the surgical securement assembly of claim 1, threading a first tail and a second tail of the securement cord through the extender tube, the connector, and the plunger lumen by utilizing the threading assembly;

exerting a desired degree of tension on the first tail and the second tail to draw taut a loop in the securement cord such that the distal end of the extender tube is positioned adjacent to structures being sorted by the cord; and maintaining a desired degree of tension on the first tail and second tail of the cord utilizing the surgical securement apparatus.

13. The method of claim 12, wherein the sorted and secured intracorporeal structures are from the group consisting of nerves, arteries, veins, tendons and muscles.

14. The method of claim 12, wherein the body of the surgical securement apparatus remains positioned outside the surgical site when the distal end of the extender tube is positioned adjacent to the structures being sorted by the securement cord.

15. The method of claim 12, wherein the connector further comprises a barbed connector for engaging and securing the extender tube with a lumen of the extender tube in communication with a lumen of the connector.

16. The method of claim 12, wherein the base of the threading assembly comprises a clasp.

17. The method of claim 16, wherein the clasp secures the threading loop.

18. The method of claim 12, wherein at least a portion of the threading assembly is positioned through a lumen of the surgical securement apparatus before threading the first tail and the second tail through a lumen of the extender tube.

19. The method of claim 12, wherein the user retracts at least a portion of the threading assembly from a lumen of the securement apparatus to thread the first tail and second tail through a lumen of the extender tube.

20. The method of claim 12, wherein the securement apparatus comprises a release button.

21. The method of claim 20, wherein when the release button is released, the first tail and second tail are secured in the surgical securement apparatus.

22. The method of claim 20, wherein when the release button is depressed, the first and second tail can be repositioned within the surgical securement apparatus.

* * * * *